United States Patent [19]
Egler

[11] Patent Number: 5,458,116
[45] Date of Patent: Oct. 17, 1995

[54] DISPLAY SYSTEM AND METHOD FOR THREE-DIMENSIONAL VECTORCARDIOGRAMS

[75] Inventor: Mark S. Egler, Cambridge, Mass.

[73] Assignee: Siemens Medical Systems, Inc., Iselin, N.J.

[21] Appl. No.: 221,142

[22] Filed: Mar. 30, 1994

[51] Int. Cl.⁶ .................................................. A61B 5/0402
[52] U.S. Cl. ............................................ 128/710; 128/699
[58] Field of Search ....................... 364/413.06; 128/699, 128/710, 696

[56] References Cited

U.S. PATENT DOCUMENTS 5,305,202  4/1994  Gallant et al. ......................... 128/696

OTHER PUBLICATIONS

"A hundred years of progress in electrocardiography 2: The rise and decline of vectorcardiography":, by Pentti M. Rautaharju, published in the Canadian Journal of Cardiology, vol. 4, No. 2, Mar. 1988, pp. 60–71.

"A study of the relationship between unipolar leads and spatial vectorcardiograms, using the panoramic vectorcardiograph", by Milnor et al., published in Circulation 1953; 7:551–555.

Primary Examiner—William E. Kamm
Assistant Examiner—Scott M. Getzow
Attorney, Agent, or Firm—Lawrence C. Edelman

[57] ABSTRACT

An apparatus and method for displaying a time history of a vectorcardiogram. The method enables a clinician to create a history of a three-dimensional vectorcardiogram from an arbitrary time axis and over an arbitrary time range. The apparatus allows the clinician to select a given viewpoint axis from a plurality of selectable viewpoint axes as well as the period of history to be displayed. The apparatus can also display multiple time histories simultaneously on the same display. This allows the display, side by side, of a traditional vectorcardiogram and the same vectorcardiogram as viewed from an arbitrary axis or time. This also enables the clinician to view a vectorcardiogram from various viewpoints simultaneously.

22 Claims, 9 Drawing Sheets

DISPLAY SYSTEM AND METHOD FOR THREE-DIMENSIONAL VECTORCARDIOGRAMS

BACKGROUND OF THE INVENTION

The present invention is an apparatus and method for displaying three-dimensional (3D) vectorcardiograms.

An electrocardiogram (ECG) is a measure of the electrical activity of the heart. It is typically measured by determining the voltage difference between a pair of electrodes placed on the body. However, because the body is a three-dimensional space, the actual ECG voltage is a three-dimensional vector in that space, and varies not only in magnitude, but also in direction. (Actually, the voltage is not even a simple vector, because it is not uniform throughout the body. Nevertheless, it is generally modeled as a vector.) Therefore, any single pair of leads measures only the voltage in the direction defined by the line between those two leads, and a set of three independent pairs of electrodes is required to measure the overall three-dimensional voltage vector. The three-dimensional ECG is usually referred to as a vectorcardiogram (VCG).

Figure 1:
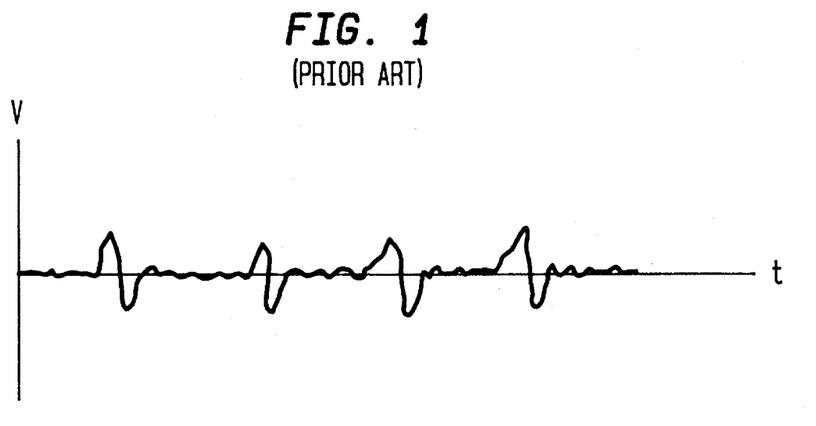
FIG. 1 is a typical prior art two-dimensional electrocardiogram.

There exist a variety of schemes for displaying ECGs. See generally P. M. Rautaharju, "A Hundred Years of Progress in Electrocardiography 2: The Rise and Decline of Vectorcardiography," *The Canadian Journal of Cardiology*, 4(2):60 (1988). The simplest and most common is shown in FIG. 1. In this two-dimensional display the horizontal axis represents time and the vertical axis represents the ECG voltage. The ECG then describes a path determined by the variation of the voltage with time. Because this display contains only one voltage dimension, it shows only a one-dimensional projection of the actual three-dimensional ECG voltage.

Figure 2:
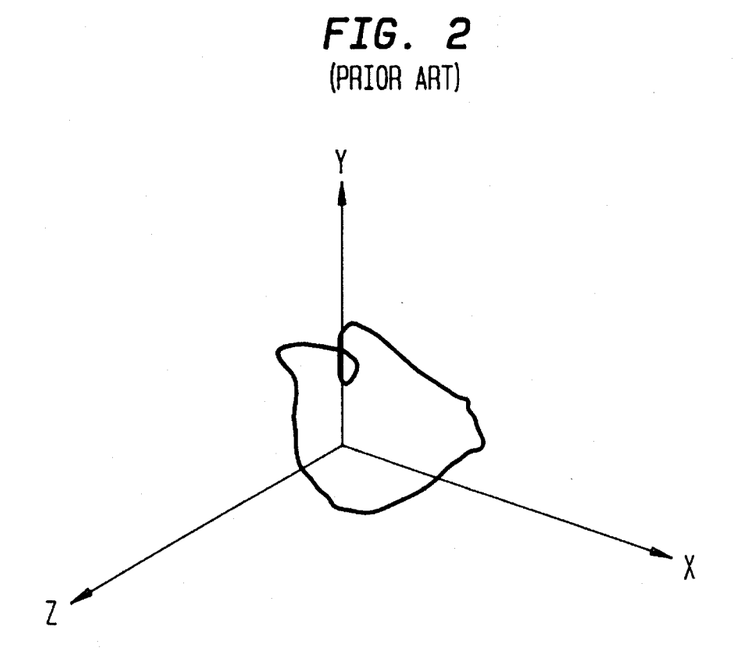
FIG. 2 is a prior art three-dimensional vectorcardiogram (projected onto the two-dimensional paper).

An alternative display is the three-dimensional vectorcardiogram (VCG). The VCG is the path traced in (three-dimensional) space by the three-dimensional ECG voltage vector. A typical VCG is shown in FIG. 2, where the three dimensions are projected into a two-dimensional display plane. Although this display presents all three spatial voltages, it contains no explicit representation of time. Although the time history of the voltage can be observed dynamically as the spatial path is traced, the VCG, once displayed, shows only the relationships among the spatial voltages. It retains no information regarding the time history of those voltages.

Each of these two prior art display formats has its advantages. The typical ECG display (FIG. 1) explicitly shows time relationships, which allows characteristics of the heart beat cycle such as the P and T waves and QRS complex to be examined. Much of the expertise of medical professionals in examining ECGs derives from their familiarity with these particular figures and patterns in the ECG. Often, however, clinicians will use several ECGs, measured along different directions in the body, to recover some of the three-dimensional information lost in a single-voltage display. All of the information in these multiple ECGs is contained in the three-dimensional VCG display (FIG. 2), which additionally shows the spatial relationships among the various voltages. However, the lack in the VCG of an explicit representation of time makes it difficult for professionals using it to benefit from their experience in interpreting time-based ECGs.

What is needed is a display that relates the single-voltage ECG to the three-dimensional VCG to allow medical professionals to benefit from their prior ECG interpretation expertise. A prior art system to show the two displays side-by-side in a static format was described in W. R. Milnor, S. A. Talbot, & E. V. Newman, "A Study of the Relationship Between Unipolar Leads and Spatial Vectorcardiograms, Using the Panoramic Vectorcardiograph," *Circulation*, 7:545 (1953). This system allowed the display of what is basically a one-dimensional cross-section through a two-dimensional view of the three-dimensional VCG. Although the system therefore displays one relationship between the two displays, it is limited to display of that single relationship. Ideally, a display should be capable of dynamically showing the transition between the two display formats, so as to make their relationships apparent. Such a display would allow medical professionals to retain the benefit of their experience in interpreting ECGs without sacrificing the additional information available in the VCG. It would also provide an ideal tool for teaching and demonstrating the relationships among the spatial and temporal elements of the heart voltage. The present invention provides these benefits.

SUMMARY OF THE INVENTION

A method for displaying a time history of a three-dimensional vectorcardiogram comprises the steps of, first defining a three-dimensional field of reference for the vectorcardiogram. Next, a time axis is selected along which to traject the vectorcardiogram history. A range of times is then specified that segments the time axis. The time history trajectory is then created by, for each of the selected time values, projecting the vectorcardiogram for that time value into a plane perpendicular to the time axis. A viewpoint axis is then selected among a plurality of selectable viewpoint axes. Finally, the time history trajectory is projected onto a display device.

The viewpoint axis of the above method may be selected such that it is perpendicular to the time axis. In this situation a single spatial dimension of the vectorcardiogram is displayed. Additionally, the viewpoint axis can be changed from a viewpoint perpendicular to the time axis whereby a single spatial dimension is displayed, to a viewpoint parallel to the time axis whereby a two dimensional projection of the vectorcardiogram is displayed.

The time axis of the above method may also be changed whereby the displayed three-dimensional vectorcardiogram is also changed. In addition, multiple time axes may be simultaneously selected so that an individual vectorcardiogram display will contain more than one time history trajectory. The time history trajectory may be expanded or contracted under user control. Further, the user may also scale the projection of the vectorcardiogram.

The method allows the simultaneous display of multiple vectorcardiograms. For instance, the method may be extended by simultaneously displaying a time history three-dimensional vectorcardiogram and a single spatial dimension of the three dimensional vectorcardiogram on the same display. This enables a split screen view of the same vectorcardiogram, displaying different views of the same information.

The method may be further extended by allowing different ranges of time values to be selected for each displayed vectorcardiogram. This enables the clinician to view and compare different periods of the same time history.

An apparatus for displaying the time history of a three-dimensional vector cardiogram in accordance with the forenoted method is also described. Various display technologies may be employed to display the vectorcardiogram.

A computer CRT display may be utilized to display a two-dimensional projection of the three dimensional vectorcardiogram. Alternatively, three-dimensional direct volume displays may be utilized, thereby providing a direct three-dimensional display of the vectorcardiogram.

The clinician using the device may select the various parameters and axes through dials, computer mice, joysticks or keyboards.

DESCRIPTION OF THE PREFERRED EMBODIMENT

The present invention provides a clear and flexible means to display the time history of three-dimensional vectorcardiograms (VCGs). The clinician can select one or more time axes along which to display the VCG time history. By enabling a clinician to view a VCG from different viewpoints, the clinician can extract the maximum amount of information from the VCG data. In prior art systems, a clinician was unable to arbitrarily select a viewpoint axis and thus lost valuable information.

The present invention then calculates and displays the history, or range of time values, of the VCG voltages in the directions orthogonal to the selected time axes. (Of course, the resulting three dimensions, one temporal and two spatial, cannot truly be shown on a two-dimensional display such as a CRT. Instead, as with the original three-dimensional VCG, it is the projection of the three dimensions into the two-dimensional plane that is displayed.)

Figure 3:
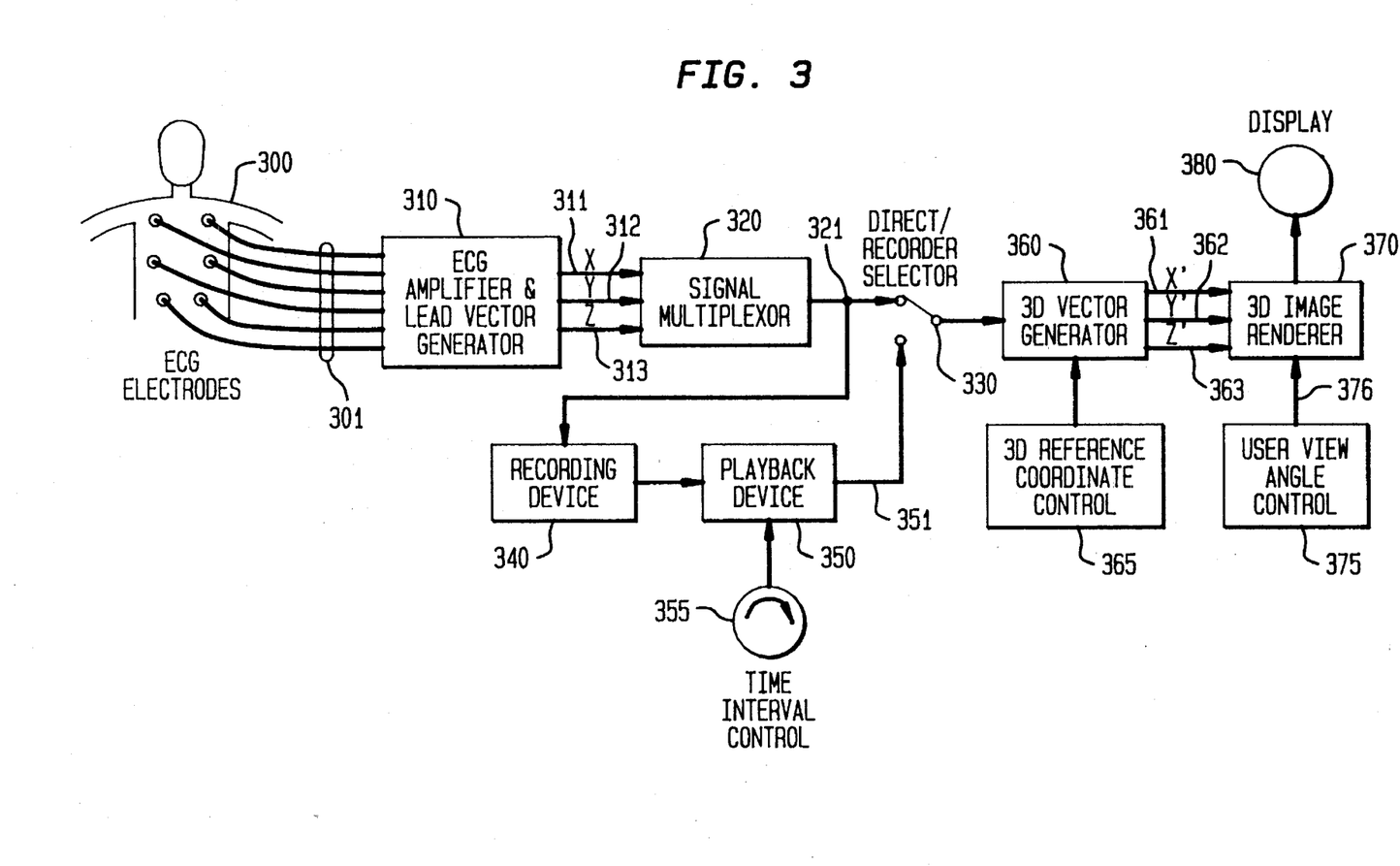
FIG. 3 is a block diagram of an vectorcardiogram system incorporating the principles of the invention.

FIG. 3 is a block diagram of a system for collecting and displaying ECG data according to the method of the invention. Raw electrical signals are sensed by a set of ECG electrodes 301, which sense and transmit the low amplitude electrical impulses from the ECG subject 300 to the ECG amplifier 310.

The ECG amplifier 310 calculates three approximately orthogonal ECG lead-vector signals 311, 312, and 313 from a set of patient surface ECG electrode voltages 301, and amplifies the voltages for reduction of noise in following circuits. The preferred method is the Frank orthogonal ECG lead system using eight electrodes to produce the three lead-vector signals X 311, Y 312 and Z 313. Alternative methods, such as computing approximations of X 311, Y 312 and Z 313 from the standard "12-lead" ECG system, or by simply selecting three of the standard 12 lead-vector signals so as to maximize the orthogonality (e.g. X=Lead I, Y=Lead aVF, Z=Lead V2), are acceptable for the purpose of the invention. These methods are well-known in ECG methodology.

The signal multiplexor 320 converts the analog signals X 311, Y 312 and Z 313 to digital signals. The signal multiplexor 320 then multiplexes the converted signals onto the output 321.

The signal 321 may pass through the direct/recorded selector 330 to the 3D vector generator for immediate processing, or may be recorded on the recorder 340 for delayed processing by the 3D vector generator 360. A recorded signal 321 is played back through playback device 350 into signal 351 which is passed through direct/recorded selector 330. This enables the system to display a prerecorded VCG signal at a more convenient time. The recorder 340 must be capable of recording 3 orthogonal ECG signals continuously for a period suitable for the intended type of ECG analysis, i.e. at least 10 seconds for a real-time ECG monitor, or from 3 to 48 hours for extended arrhythmia analysis purposes. The playback device 350 must playback the recorded ECG signals for a desired time interval, preferably simultaneously with the recording process. The time interval control 355 controls the timing of the playback device 350.

The 3D vector generator 360 receives either real time ECG data 321 or prerecorded ECG data 351 through the direct/recorded selector 330. The 3D vector generator 360 takes as input the set of X, Y and Z signals and performs a 3D coordinate rotation about a user-controlled axis through the origin, by calculating the corresponding coordinates X' 361, Y' 362 and Z' 363 in the rotated frame of reference using the well-known coordinate transformation formula for rotation. The preferred embodiment for the vector generator 360 is a digital computer. The user-controlled axis is selected and modified by the 3D reference coordinate control 365, which in the preferred embodiment is a joystick, mouse or trackball.

The transformed signals, X' 361, Y' 362 and Z' 363 are fed into the 3D image renderer 370. The image rendered takes as input the set of X' 361, Y' 362 and Z' 363 rotated ECG signals for a desired time interval T1 to T2 and a set of one or more user-controlled 3D reference time axis vectors 376 to generate one or more VCG trajectories for display. The user-controlled 3D reference time axis vectors are selected by the user view angle control 375 which may be a keyboard or joystick device. A VCG trajectory is the set of 3D coordinate values made up of either all 3 ECG signals, or any pair of ECG signals (e.g. X and Y) with the third dimension replaced by a linear representation of the corresponding time values. Four such 3D trajectories are possible: X'Y'Z', X'Y'T, X'Z'T, and Y'Z'T each conveying different VCG information.

Finally, the VCG trajectories are rendered on a display 380 for viewing by the clinician, by any means of rendering the 3D trajectories into an image that allows the viewer to perceive their three-dimensional nature. Examples of such displays include a 2D projection onto a flat screen, with dynamic user control of viewing angle allowing hand-eye visual feedback, or other methods to provide the 3D depth cues, a stereoscopic display consisting of two such 2D projections, visible by viewers with normal stereoscopic vision, a Direct Volume Display Device (DVDD) which can render a true 3D image into the space defined by the volume-of-rotation of a rotating or oscillating mirror. Such DVDDs can be viewed by a number of simultaneous viewers in different positions, and reproduce parallax effects of a moving viewer. See generally T. E. Clifton, F. C. Wefer, "*Direct Volume Display Devices*," IEEE Computer Graphics and Applications Number 13:57–65, July 1993.

Figure 4:
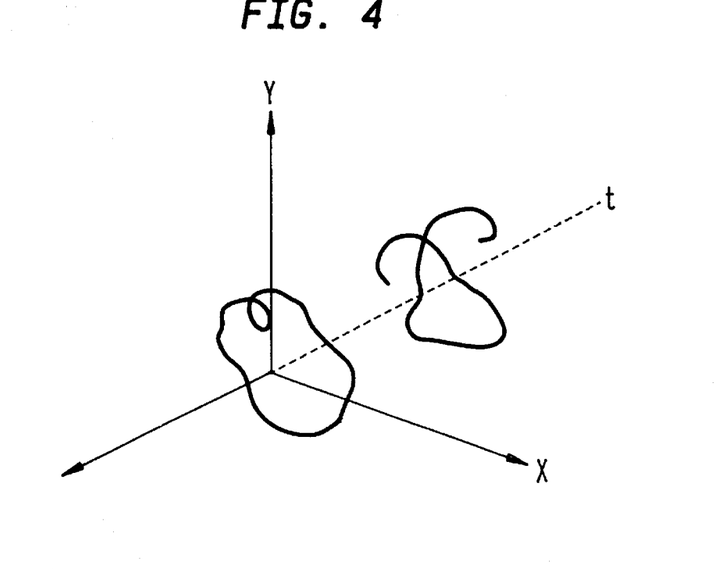
FIG. 4 shows a three-dimensional vectorcardiogram display, together with one cycle of a two-dimensional time history displayed according to the invention.
Figure 5:
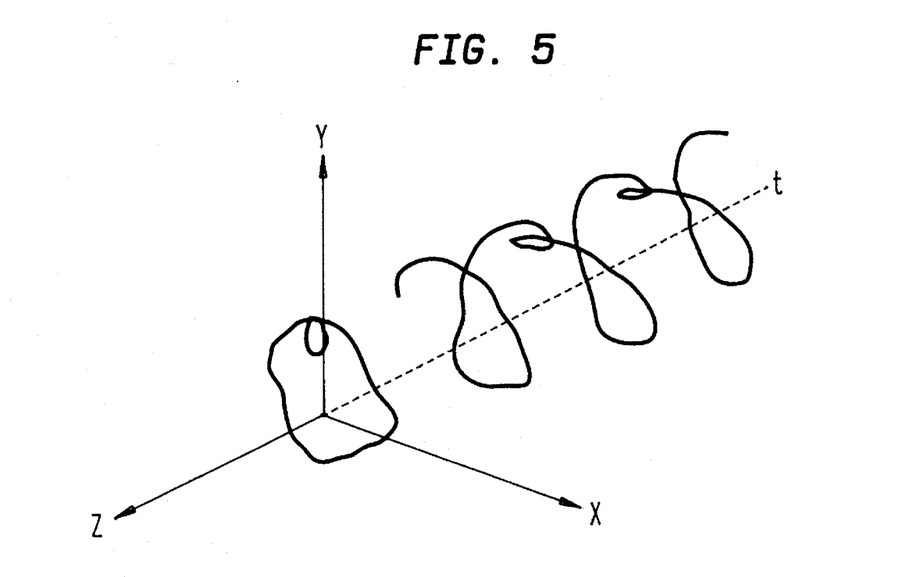
FIG. 5 shows a three-dimensional vectorcardiogram display, together with several cycles of a two-dimensional time history displayed according to the invention.

As an illustration of the signal displayed, consider FIG. 5. In this Figure, the original spatial dimensions are x, y, and z. A time axis t is selected, in this case parallel to the z axis. The two spatial dimensions to be displayed in the time history are therefore x and y. The display is then created by projecting the three-dimensional VCG along the time axis for the time range of interest. This typically produces a figure that spirals around the time axis. A single loop of the spiral is shown in FIG. 4; FIG. 5 shows several loops of the spiral. The following paragraphs provide a detailed description of the operation of the invention.

Operation of the Invention

The selection of a time axis for display of the VCG time history is arbitrary. The clinician designates the time axis by reference to a three-dimensional coordinate system used in displaying the vectorcardiogram. This allows the VCG display to be used to investigate the time history along any particular axis of interest to the clinician. This VCG coordinate system typically consists of three axes oriented relative to the torso: left-right, up-down, and anterior-posterior. In FIG. 5, these axes are represented as the x, y, and z axes, respectively. The time axis is then selected by defining a three-dimensional vector in this VCG coordinate system. For example, in FIG. 5, where the time axis is parallel to, but in the opposite direction of, the z axis, the three-dimensional vector defining it is (0, 0, −1).

A particular time range of the VCG history to be displayed must also be selected. If the data of the VCG to be displayed are available for a particular time range, say $t_1$ to $t_2$, then any subset of that range may be used. The range selected is then mapped to a designated portion of the time axis. The portion of the time axis to be used is designated by specifying its endpoints, again in the VCG coordinate system. The time range is then scaled to conform to the selected portion of the time axis. The time range can also be specified by reference to the present time if, for example, it is desired to continuously display the last 10 seconds of the VCG (i.e. $t_{present}-10$ to $t_{present}$).

Figure 6:
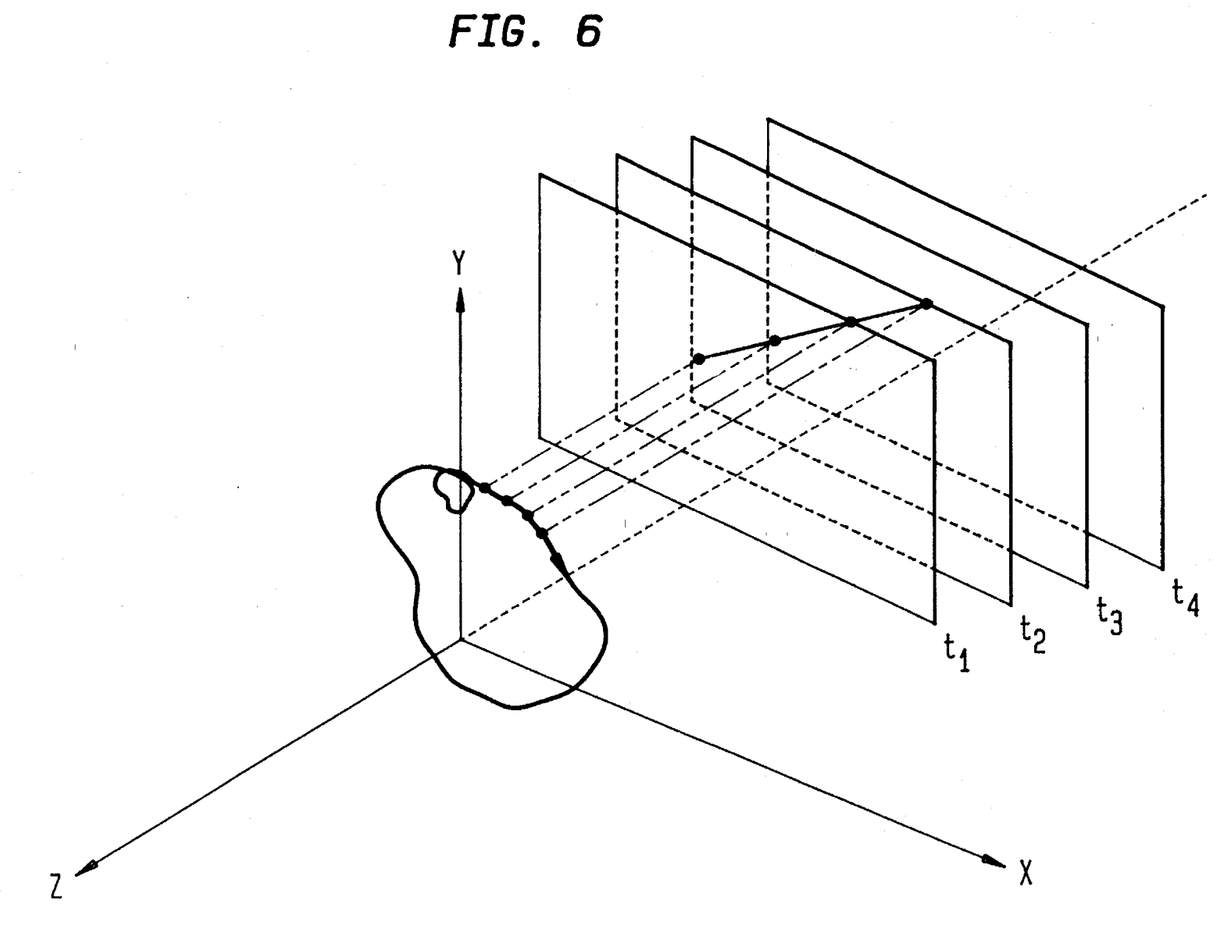
FIG. 6 shows a series of projections of the three-dimensional vectorcardiogram into successive planes perpendicular to the time axes.

Determination of the time history is accomplished by projecting the three-dimensional VCG into successive planes perpendicular to the selected time axis. For each time in the selected range, a plane perpendicular to the time axis at that point is constructed. The display point of the VCG time history at that time is then determined by projecting the VCG into that plane. Repetition of this process for each time value creates a time history trajectory. A graphical depiction of this process is shown in FIG. 6 for times $t_1$, $t_2$, $t_3$, and $t_4$. As times are layered, the display converges on a continuous time history trajectory as illustrated in FIG. 5.

Figure 7:
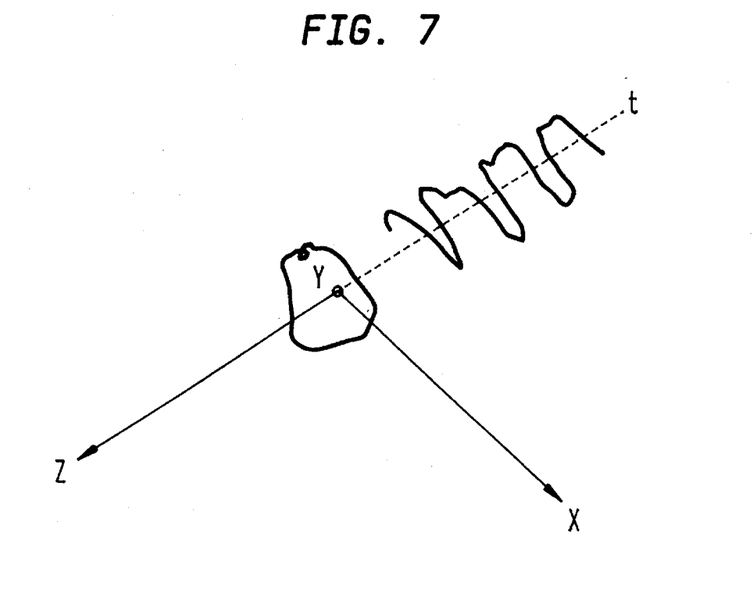
FIG. 7 is the display of FIG. 5, viewed along the y axis.

Finally, the perspective from which the display is viewed is also selected by the clinician. Different viewpoints, of course, result in different displays. For example, FIG. 7 shows the VCG of FIG. 5, but viewed along the viewer axis which in this case is the y axis. Selection of the viewpoint axis is accomplished in the same manner as selection of the time axis, by designating a vector in the VCG coordinate system. In FIG. 7, then, where the display is viewed in the direction of the negative y axis, the viewpoint axis is defined as (0, −1, 0).

Display of the time history trajectory along the selected time axis is then made by projecting the display points of the trajectory into a display plane perpendicular to the viewpoint axis. This results in a two-dimensional representation of the three dimensions (two spatial and one temporal) of the time history.

Features of the Invention

It can be seen from the description of the invention that it allows a great deal of flexibility. Through selection of the time and viewpoint axes, a wide variety of displays can be created.

For example, depending on the method chosen for defining the axes, it is possible to controllably or even continuously rotate the display. In one embodiment of the invention, the time and viewpoint axes are designated by defining static vectors. This can be done, as described previously, by using a numerical designation of the vector. Thus, a time vector defined as (0, 0, 1) is a vector along the z axis. The designations of the numerical values for the vector components can be accomplished either through keyboard entry or through an analog device such as a set of dials, a joystick or computer mouse controlled by the user. If, for example, dials are used, the axis can be selectively or continuously changed by rotating the dials. This then allows a preferred embodiment of the invention to provide controllable motion of one or both of the time and viewpoint axes.

Figure 9A:
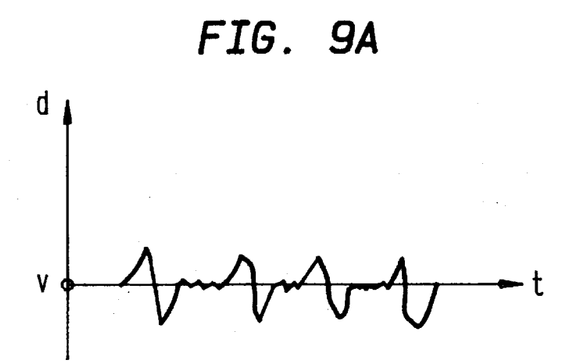
FIGS. 9a–9d are a series of perspective views, from different sequential viewpoints, of a two-dimensional time history displayed according to the invention.
Figure 9B:
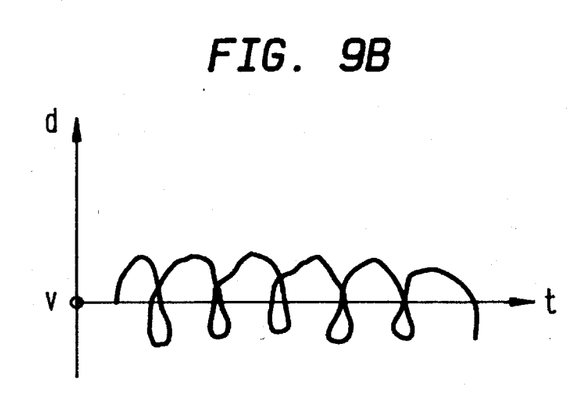
Figure 9C:
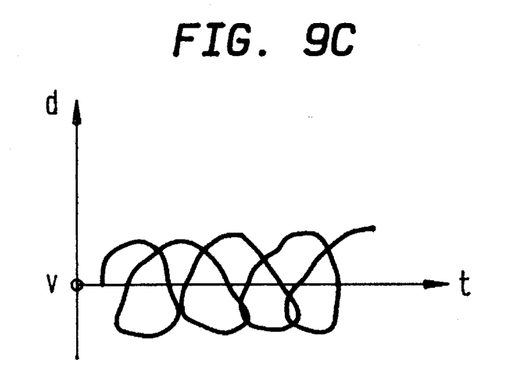
Figure 9D:
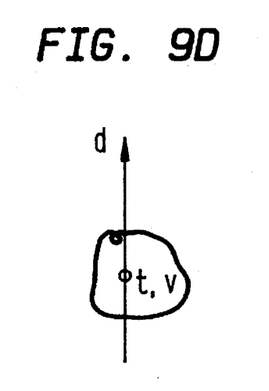

Change of the viewpoint axis allows the display to be rotated as a unit (i.e., with the relationship between the time axis and the vectorgram coordinate axis remaining the same). This allows the clinician to view the display from various perspectives, some of which may show particular characteristics of the ECG better than others. It also allows the time histories of the display to be viewed in a continuous and real-time transition from a perspective directly along the time axis-from which they appear exactly as the three-dimensional purely spatial VCG (as in FIG. 9d, to be described)-to perspectives perpendicular to the time axis-from which only a single voltage dimension is visible as found in a prior art two-dimensional electrocardiogram (as in FIG. 9a, to be described). The implications of this capability are more clear when one considers a specific example.

Figure 8:
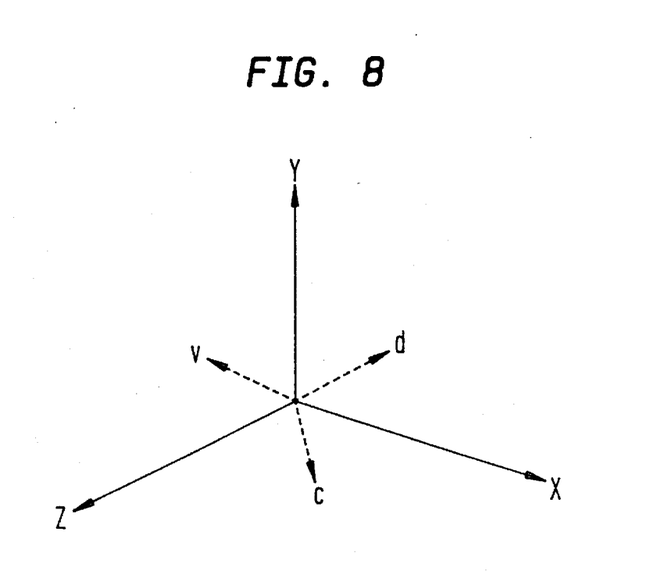
FIG. 8 shows the three-dimensional vectorcardiogram coordinate system with time and viewpoint axes chosen to produce a two-dimensional cardiogram such as FIG. 1.

FIG. 8 shows a particular selection of voltage, time, and viewpoint axes. Assume that it is desired to display a traditional two-dimensional ECG like that in FIG. 1. Assume further that it is the display of the voltage in direction d that is desired. By selecting a time axis t perpendicular to direction d, and then selecting a viewpoint v perpendicular to both d and t, as shown in FIG. 8, the traditional ECG along d is displayed. That is, this selection of axes produces a display, in the form shown in FIG. 1, of the voltage along the vector d in the body.

FIG. 9 shows the displays that can be produced by continuously rotating the viewpoint axis. In FIG. 9a, the viewpoint axis is in direction v shown in FIG. 8. In FIG. 9d, the viewpoint axis is the same as the time axis t in FIG. 8. In FIGS. 9b and 9c, the viewpoint axes are at intermediate positions between those in FIGS. 9a and 9d. It can be seen that a transition from FIG. 9a through FIGS. 9b and 9c to FIG. 9d effects a transition from the traditional two-dimensional ECG of FIG. 1 to the three-dimensional VCG. It therefore provides a means for the clinician to relate the two-dimensional ECG characteristics with which she is familiar to the VCG.

Rotation of the time axis, rather than the viewpoint axis, has a different but also useful effect. The selection of a particular time axis displays the voltages perpendicular to that axis. Each of those voltages represents the voltage along a particular vector in the body and thus the voltage that would be measured by a particular positioning of electrodes on the body. Therefore, rotation of the time axis provides an effective rotation of the voltage vector, much as a physical relocation of electrodes on the body would do. It allows the clinician to view the voltage of any particular lead location or the voltage along a vector that is intermediate between lead locations.

Figure 10:
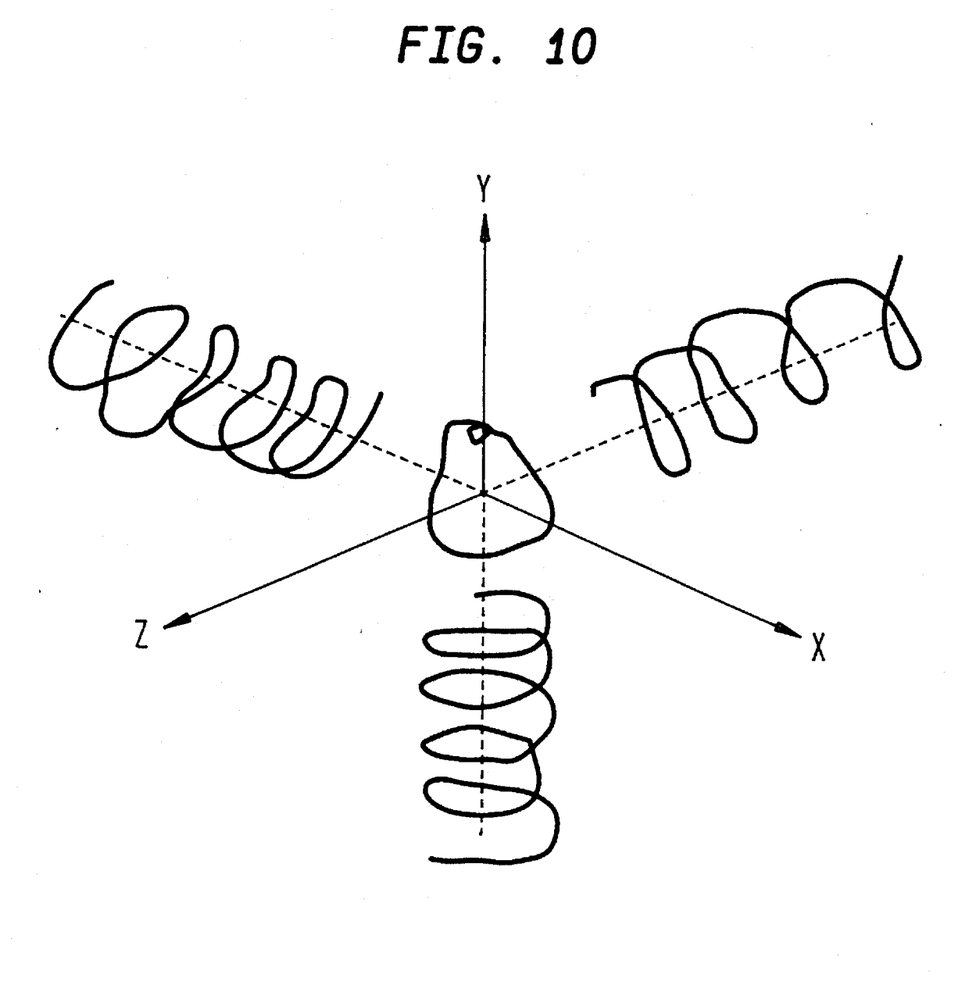
FIG. 10 shows a three-dimensional vectorcardiogram display, together with several cycles of three two-dimensional time histories displayed according to the invention.
Figure 11:
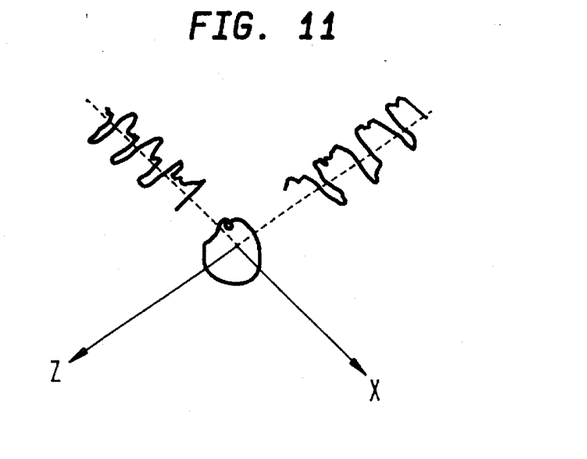
FIG. 11 is the display of FIG. 10, viewed along the y axis.
Figure 12A:
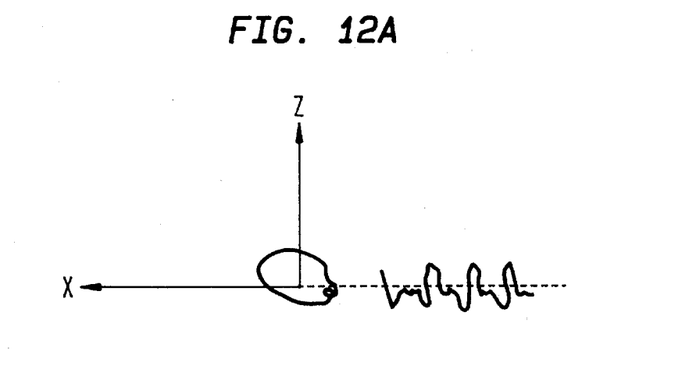
FIGS. 12a and 12b show the time history displays of FIG. 10, positioned with their time axes aligned.
Figure 12B:
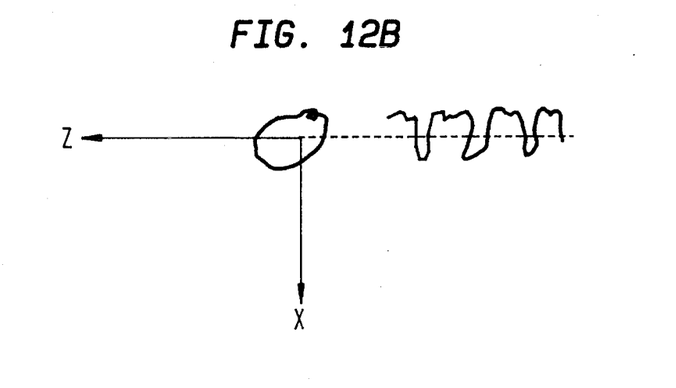
Figure 13A:
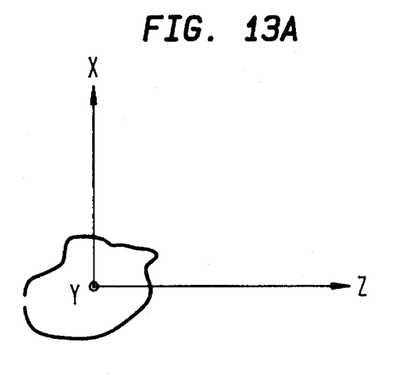
FIGS. 13a–13b, 13c–13d, and 13e–13f show three time histories, each viewed from a perpendicular to its time axis, on the right and with a display of the three-dimensional vectorcardiogram viewed along its time axis, on the left.
Figure 13B:
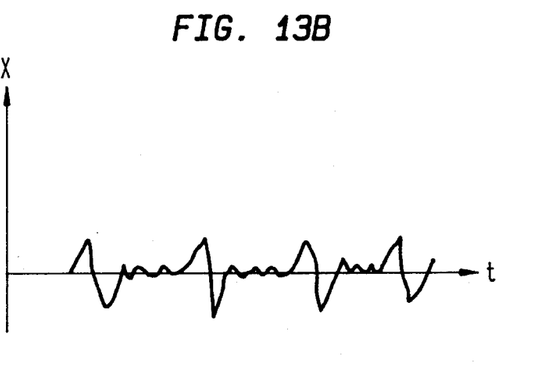
Figure 13C:
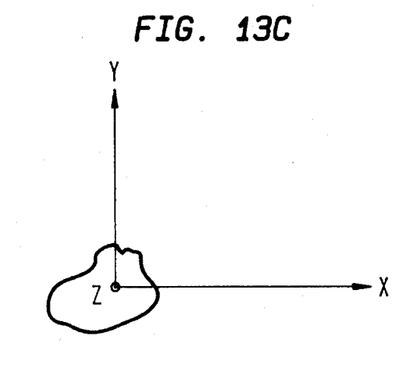
Figure 13D:
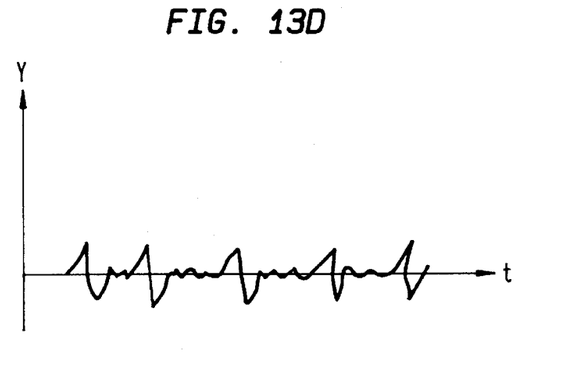
Figure 13E:
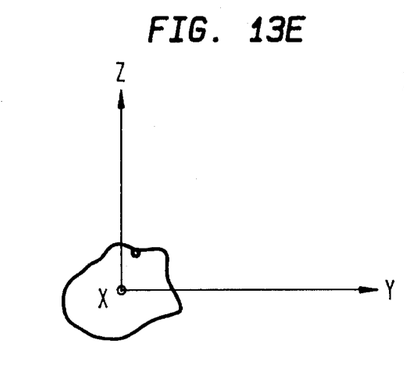
Figure 13F:
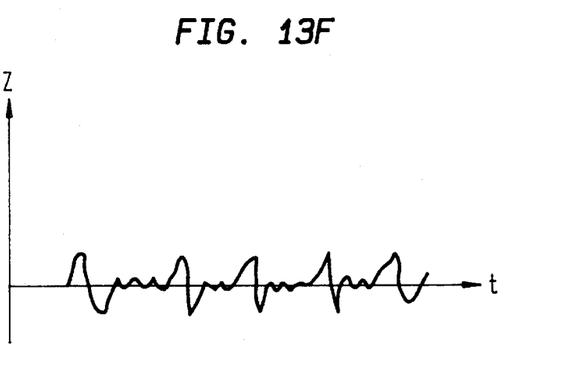

Another feature of the invention is to provide displays along multiple time axes simultaneously. FIG. 10 shows three time histories along each of three orthogonal axes. Any number of axes could be chosen, of course, and they need not be orthogonal. Another possibility is shown in FIG. 11, where two perpendicular time axes are chosen, and they are viewed along a third orthogonal axis. Because it may be more useful to view these displays with the two time axes aligned, they can be displayed as shown in FIGS. 12a and 12b, which duplicate the two portions of the display in FIG. 11. Alternatively, to display multiple time histories, a display like that shown in FIG. 13 can be created, where three single-voltage ECGs (FIGS. 13a, 13c, and 13e) are accompanied by their respective three-dimensional VCGs (FIGS. 13a, 13c, and 13f) as viewed along the same time axis. The system can display all of these views simultaneously, or just a selected subset of these views.

Thus, there has been shown and described a novel display system for three-dimensional vectorcardiograms which satisfies all the objects and advantages sought therefore. Many changes, modifications, variations and other uses and applications of the subject invention will, however, become apparent to those skilled in the art after considering this specification and its accompanying drawings, which disclose preferred embodiments thereof. All such changes, modifications, variations and other uses and applications which do not depart from the spirit and scope of the invention are deemed to be covered by this patent, which is limited only by the claims which follow as interpreted in light of the foregoing description.

I claim:

1. A method for allowing a user to controllably display at least one time history of a three-dimensional vectorcardiogram by displaying at least one time history trajectory, comprising:

defining a three-dimensional field of reference for the vectorcardiogram;

defining at least one time axis in the vectorcardiogram field of reference;

defining a range of time values;

assigning the range of time values to a segment of each at least one time axis;

creating a time history trajectory for each at least one time axis by, for each time value in the defined range of time values, projecting the vectorcardiogram onto a plane perpendicular to the at least one time axis at the time value;

user selection of a given viewpoint axis from a plurality of selectable viewpoint axes in the vectorcardiogram field of reference; and displaying each at least one time history trajectory from the selected viewpoint axis.

2. The method of claim 1 wherein said creating step creates a plurality of time histories which are simultaneously displayed; and said user selection step selects a different viewpoint axis for each time history displayed.

3. The method of claim 2, wherein after the step of displaying each time history trajectory, said user selection step controllably changes each selected viewpoint axes, whereby the perspective from which each time history is displayed is also controllably changed.

4. The method of claim 1 wherein said creating step creates a plurality of time histories which are simultaneously displayed; and said defining a range step defines a same range of time values for each time history displayed.

5. The method of claim 1 wherein said displaying step comprises projecting the time history trajectory onto a display plane perpendicular to the viewpoint axis.

6. The method of claim 1 wherein said displaying step comprises projecting the time history trajectory into a three-dimensional volume; and said user selection step comprises user movement about said three-dimensional volume.

7. The method of claim 1 wherein said step of defining a time axis in the vectorcardiogram field of reference comprises selecting a given time axis among a plurality of user selectable time axes.

8. The method of claim 7 wherein said step of defining a time axis in the vectorcardiogram field of reference comprises user selection of the different time axes for each time history displayed.

9. The method of claim 7, wherein after the step of displaying each time history trajectory, a user control step is provided for controllably changing each time axis, whereby projection of each time history trajectory is also controllably changed.

10. The method of claim 1 wherein said step of defining a range of time values comprises user selection of a range of time values.

11. The method of claim 1 wherein after said step of displaying each at least one time history trajectory, at least one of the at least one time axis is controllably changed, whereby projection of the time history trajectory is also controllably changed.

12. The method of claim 1, wherein after the step of displaying each at least one time history trajectory, said user selection step changes the selected viewpoint axes, whereby the perspective from which the time history is displayed is also changed.

13. The method of claim 1, wherein said step of defining a three-dimensional field of reference comprises scaling the three-dimensional field of reference by a user selectable scaling-factor.

14. The method of claim 1, wherein said step of displaying each time history trajectory comprises scaling the time history trajectory by a user selected zooming factor so that the user can increase or decrease the size of the displayed time history trajectory.

15. An apparatus for displaying a time history of a three-dimensional vectorcardiogram by displaying at least one time history trajectory, comprising:
 a computing device, coupled to receive a three-dimensional vectorcardiogram, for calculating for sequential time values, a projection of the vectorcardiogram onto a plane perpendicular to a given time axis in a reference orientation at the sequential time values, thereby creating the at least one time history trajectory;
 a first user selection entry device, coupled to said computing device, for enabling a user to select a given viewpoint axis relative to the reference orientation among a plurality of user-selectable viewpoint axes; and
 a display device, coupled to said computing device, and responsive to said at least one created time history trajectory, for displaying said time history trajectory.

16. The apparatus of claim 15 additionally comprising a second user selection entry device, coupled to said computing device, for enabling the user to select the given time axis relative to the reference orientation among a plurality of user-selectable time axis.

17. The apparatus of claim 16 additionally comprising a third user selection entry device, coupled to said computing device, for enabling the user to assign a predetermined range of time sequential values to a segment of the given time axis.

18. The apparatus of claim 15 wherein the display device comprises a direct volume display device.

19. The apparatus of claim 15 wherein the display device comprises a video display screen for showing a projection of the time history into a plane perpendicular to the viewpoint axis.

20. The apparatus of claim 15, wherein said computing device creates a plurality of time history trajectories, each time history trajectory having a different time axis, and said display device is coupled to be responsive to said created plurality of time history trajectories, for causing them to be simultaneously displayed.

21. The apparatus of claim 20, wherein the first user selection device selects a range of sequential viewpoint axes to be used for sequential display of each of said time history trajectories, said range extending from a viewpoint axis perpendicular to the time axis, whereby a single spatial dimension of the three-dimensional vectorcardiogram is displayed, to a viewpoint axis parallel to the time axis, whereby a two-dimensional projection of the three-dimensional vectorcardiogram is displayed.

22. The apparatus of claim 15 wherein the first user selection device selects a range of sequential viewpoint axes to be used for sequential display of said time history, said range extending from a viewpoint axis perpendicular to the time axis, whereby a single spatial dimension of the three-dimensional vectorcardiogram is displayed, to a viewpoint axis parallel to the time axis, whereby a two-dimensional projection of the three-dimensional vectorcardiogram is displayed.

\* \* \* \* \*